US006420386B1

(12) United States Patent
Cordi et al.

(10) Patent No.: US 6,420,386 B1
(45) Date of Patent: Jul. 16, 2002

(54) ARYL OR HETEROARYL QUINOLYLPHOSPHONIC ACID COMPOUNDS

(75) Inventors: Alex Cordi, Suresnes; Patrice Desos, Courbevoie; Pierre Lestage, La Celle Saint Cloud, all of (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/783,192

(22) Filed: Feb. 14, 2001

(30) Foreign Application Priority Data

Feb. 18, 2000 (FR) .............................. 00.02013

(51) Int. Cl.[7] .................. A61K 31/4709; C07F 9/6578; C07D 215/02
(52) U.S. Cl. .................. 514/311; 514/312; 546/21; 546/156; 546/157
(58) Field of Search .............. 546/152, 156, 546/157, 21; 514/311, 312

(56) References Cited

U.S. PATENT DOCUMENTS 5,342,946 A * 8/1994 Hamilton .................. 546/23
5,536,709 A * 7/1996 Cordi et al. ............. 514/82

* cited by examiner

*Primary Examiner*—Alan L. Rotman
*Assistant Examiner*—Rita Desai
(74) *Attorney, Agent, or Firm*—Hueschen and Sage; G. Patrick Sage

(57) ABSTRACT

The invention relates to a compound of formula (I):

wherein:

$R^1$ represents halogen or a group $CF_3$, $R^2$ represents aryl or heteroaryl, $R^3$ and $R^4$ are as defined in the description and methods for using the same.

10 Claims, No Drawings

ARYL OR HETEROARYL QUINOLYLPHOSPHONIC ACID COMPOUNDS

FIELD OF THE INVENTION

The present invention relates to new aryl or heteroaryl quinolylphosphonic acid compounds, and to compositions containing them.

DESCRIPTION OF THE PRIOR ART AND BACKGROUND OF THE INVENTION

The prior art describes compounds that are capable of countering the excitatory and toxic effects of the excitatory amino acids (EAA) by blocking the initial activation of the AMPA (α-amino-3-hydroxy-5-methyl-4-isoxazolepropionic acid)/kainate receptor (EP 0 640 612). Their usefulness is accordingly recognised for inhibiting pathological phenomena, especially neurotoxic phenomena associated with hyperactivation of the neurotransmission paths to the excitatory amino acids.

The Applicant has discovered new compounds of novel structure that have more powerful non-NMDA antagonist properties than do the compounds of the prior art. The compounds are therefore new and are potential powerful therapeutic agents for the acute, and also chronic, treatment of neurological and psychological disorders involving those amino acids, for example degenerative disorders such as cerebrovascular accident, cerebral or spinal traumatism, epilepsy, chronic neurodegenerative diseases such as Alzheimer's disease, schizophrenia, lateral amyotrophic sclerosis or Huntington's chorea.

DETAILED DESCRIPTION OF THE INVENTION

The present invention relates more especially to compounds of formula (I):

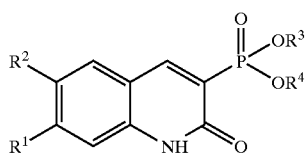

wherein:
- $R^1$ represents a halogen atom or a trifluoromethyl group,
- $R^2$ represents an aryl or heteroaryl group,
- $R^3$ and $R^4$, which may be identical or different, represent a hydrogen atom or an alkyl, cycloalkyl, aryl or arylalkyl group or a group

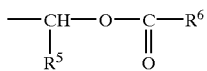

(wherein $R^5$ and $R^6$, which may be identical or different, represent a hydrogen atom or an alkyl, cycloalkyl or aryl group), it being understood that:
- "alkyl" is understood to mean a linear or branched alkyl group containing from 1 to 6 carbon atoms,
- "cycloalkyl" is understood to mean a cyclic alkyl group containing from 3 to 8 carbon atoms,
- "aryl" is understood to mean the groups phenyl, naphthyl or biphenyl, it being possible for those groups to be unsubstituted or substituted by from 1 to 3 groups selected from alkyl, cycloalkyl, alkoxy, polyhaloalkyl, cyano, nitro, amino, alkylamino, dialkylamino, $SO_2NR^7R^8$ (wherein $R^7$ and $R^8$, which may be identical or different, represent a hydrogen atom or an alkyl, cycloalkyl or aryl group) and halogen atoms,
- "heteroaryl" is understood to mean any mono- or bi-cyclic aromatic group containing from 5 to 10 ring atoms and containing from 1 to 3 hetero atoms selected from oxygen, nitrogen and sulphur, it being possible for the heteroaryl to be attached to the benzene ring that carries it by a carbon atom or by a nitrogen atom when it has one, and for it to be unsubstituted or substituted by from 1 to 3 groups selected from alkyl, cycloalkyl, alkoxy, polyhaloalkyl, cyano, nitro, amino, alkylamino, dialkylamino, $SO_2NR^7R^8$ (wherein $R^7$ and $R^8$ are as defined hereinbefore) and halogen atoms, their enantiomers and diastereoisomers and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc.

Among the pharmaceutically acceptable bases there may be mentioned by way of non-limiting example sodium hydroxide, potassium hydroxide, triethylamine, tert-butylamine, etc.

The preferred compounds of the invention are compounds of formula (I) wherein $R^1$ represents a chlorine atom or a group $CF_3$.

The preferred groups $R^2$ are phenyl, naphthyl or biphenyl, those groups being unsubstituted or substituted, more especially by a halogen atom or by a group $CF_3$, $NO_2$, alkyl or $SO_2NH_2$, or pyrrole or thiophene groups.

More preferably, the invention relates to compounds of formula (I) wherein $R^3$ and $R^4$ simultaneously represent a hydrogen atom.

More especially still, the invention relates to compounds of formula (I) which are:

{7-chloro-2-oxo-6-[4-(trifluoromethyl)phenyl]-1,2-dihydro-3-quinolyl}-phosphonic acid

[7-chloro-6-(4-methylphenyl)-2-oxo-1,2-dihydro-3-quinolyl]phosphonic acid.

The invention relates also to a process for the preparation of compounds of formula (I), characterised in that there is used as starting material a compound of formula (II):

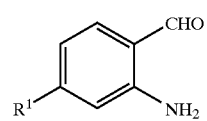

wherein $R^1$ is as defined for formula (I), which is condensed, in the presence of a base, such as, for example, pyridine, with a compound of formula (III):

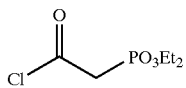
(III)

to yield a compound of formula (IV):

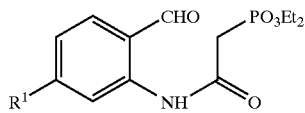
(IV)

wherein $R^1$ is as defined hereinbefore, which is cyclised in the presence of a catalytic amount of piperidine to obtain a compound of formula (V)

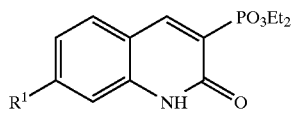
(V)

wherein $R^1$ is as defined hereinbefore, which is subjected to a mixture of nitric acid and sulphuric acid to yield a compound of formula (VI):

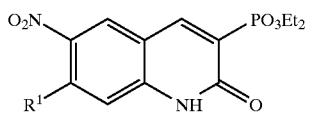
(VI)

wherein $R^1$ is as defined hereinbefore, which is reduced using palladium-on-carbon in the presence of hydrogen or iron in a dilute alcoholic medium to yield a compound of formula (VII):

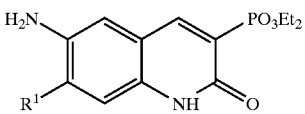
(VII)

wherein $R^1$ is as defined hereinbefore, which is converted by the action of $NaNO_2$ and $HBF_4$ to the corresponding diazonium fluoroborate salt of formula (VIII):

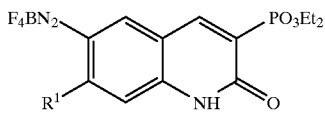
(VIII)

wherein $R^1$ is as defined hereinbefore, which is condensed in the presence of palladium with a boronic acid compound of formula (IX):

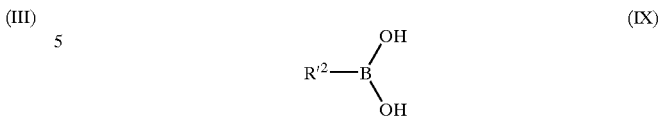
(IX)

wherein $R'^2$ represents an aryl or heteroaryl group as defined for formula (I), the heteroaryl group being attached to the boron atom by a carbon atom, to yield a compound of formula (I/a), a particular case of the compounds of formula (I):

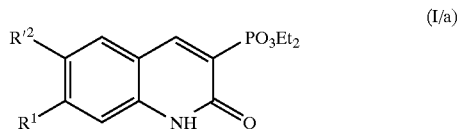
(I/a)

wherein $R^1$ and $R'^2$ are as defined hereinbefore, or which compound of formula (VII) is subjected to the action of 2,5-dimethoxytetrahydrofuran to yield a compound of formula (I/b), a particular case of the compounds of formula (I):

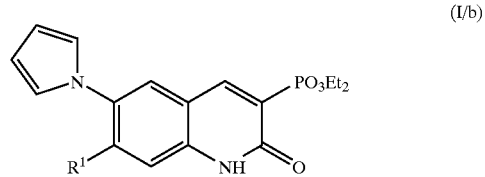
(I/b)

wherein $R^1$ is as defined hereinbefore, which compounds of formulae (I/a) and (I/b) may be partially or totally deprotected in the presence of, for example, trimethylsilane bromide to yield a compound of formula (I/c), a particular case of the compounds of formula (I):

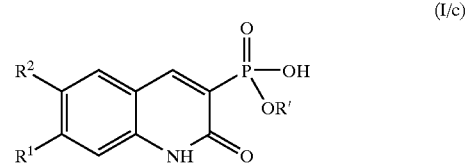
(I/c)

wherein $R^1$ and $R^2$ are as defined hereinbefore and $R'$ represents a hydrogen atom or an ethyl group, which may be condensed with a compound of formula (X):

(X)

wherein R" represents an alkyl, aryl or arylalkyl group or a group

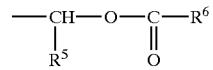

(wherein $R^5$ and $R^6$ are as defined hereinbefore), to obtain a compound of formula (I/d), a particular case of the compounds of formula (I):

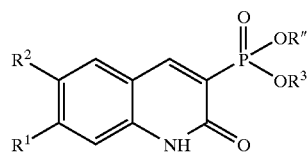

wherein $R^1$, $R^2$, $R^3$ and $R''$ are as defined hereinbefore, which compounds of formulae (I/a) to (I/d) constitute the totality of the compounds of formula (I), and can be purified according to a conventional separation technique, are converted, if desired, into their addition salts with a pharmaceutically acceptable acid or base, and separated, where appropriate, into their isomers according to a conventional separation technique.

The compounds of the invention have very valuable pharmacological properties since they are powerful inhibitors of the AMPA receptor, and they are moreover selective since they do not affect the NMDA receptor and therefore do not have any of the side-effects described for NMDA antagonists. The use of those compounds as inhibitors of pathological phenomena associated with hyperactivation of the neurotransmission paths to the excitatory amino acids will therefore be particularly appreciated in the acute, and especially chronic, treatment of neurological and psychological disorders involving those amino acids, for example degenerative disorders such as cerebrovascular accident, cerebral or spinal traumatism, epilepsy, chronic neurodegenerative diseases such as Alzheimer's disease, schizophrenia, lateral amyotrophic sclerosis or Huntington's chorea.

The present invention relates also to pharmaceutical compositions comprising as active ingredient at least one compound of formula (I) alone or in combination with one or more pharmaceutically acceptable excipients.

Among the pharmaceutical compositions according to the invention, there may be mentioned more especially those that are suitable for oral, parenteral, nasal, per- or transcutaneous, rectal, perlingual, ocular or respiratory administration and especially tablets or dragees, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, or any associated treatments and ranges from 50 mg to 10 g per 24 hours in 1 or more administrations.

The following Examples illustrate the invention and do not limit it in any way.

EXAMPLE 1

(7-Chloro-2-oxo-6-phenyl-1,2-dihydro-3-quinolyl)-phosphonic acid diethyl ester

Step A: [(5-Chloro-2-formyl-phenylcarbamoyl)methyl]phosphonic acid diethyl ester Pyridine (3.7 ml, 45.7 mmol) is added to a solution of 2-amino-4-chloro-benzaldehyde (6.18 g, 39.7 mmol) in 170 ml of anhydrous toluene, followed dropwise by a solution of chlorocarbonylmethylphosphonic acid diethyl ester (9.8 g, 45.7 mmol) in 15 ml of anhydrous toluene whilst maintaining the reaction mixture at a temperature of less than 30° C. When the addition is complete, the mixture is stirred for 1 hour at room temperature. The reaction mixture is washed several times with water and then with a 1N HCl solution, and then again with water. Finally the mixture is washed with an aqueous saturated NaCl solution. The organic phase is dried over $MgSO_4$, and filtration is carried out, followed by evaporation to obtain the expected crude product in the form of an orange oil. The crude product is used in the following step.

Step B: (7-Chloro-2-oxo-1,2-dihydro-3-quinolyl)phosphonic acid diethyl ester

In a round-bottomed flask on which there is mounted a Dean-Stark apparatus there is refluxed for 4 hours, with vigorous stirring, all of the compound obtained in Step A dissolved in 300 ml of toluene and 0.3 ml of piperidine. The batch is left to crystallise at room temperature and the resulting pale yellow solid corresponding to the title product is filtered off.

Melting point: 210–213° C.

Elemental microanalysis:

|  | C % | H % | N % | Cl % |
|---|---|---|---|---|
| calculated | 49.46 | 4.79 | 4.44 | 11.23 |
| found | 49.77 | 4.78 | 4.46 | 11.63 |

Step C: (7-Chloro-6-nitro-2-oxo-1,2-dihydro-3-quinolyl)phosphonic acid diethyl ester 55 ml of nitric acid are added dropwise to a solution of 55 ml of 96% sulphuric acid cooled in an ice bath, and then the compound obtained in Step B (14.7 g, 46.6 mmol) is added in portions whilst maintaining the temperature at less than or equal to 5° C. When the addition is complete, stirring is continued for 15 minutes and then the ice bath is withdrawn and the reaction mixture is brought to room temperature over a period of about 1 hour 30 minutes. The solution is poured into ice and the precipitate is stirred to obtain a filterable solid. Filtration is carried out, followed by washing with water to neutrality and drying in vacuo. The solid is suspended in 210 ml of ethanol at reflux ; the batch is left to cool and filtered to obtain the title compound after drying.

Melting point: 258–262° C.

Elemental microanalysis:

|  | C % | H % | N % | Cl % |
|---|---|---|---|---|
| calculated | 43.29 | 3.91 | 7.77 | 9.83 |
| found | 43.33 | 4.06 | 7.60 | 9.70 |

Step D: (6-Amino-7-chloro-2-oxo-1,2-dihydro-3-quinolyl)phosphonic acid diethyl ester A suspension of the compound obtained in Step C (7.0 g, 19.4 mmol), powdered iron (10.8 g, 194 mmol) and ammonium chloride (10.4 g, 194 mmol) is stirred at reflux for 1 hour in a mixture of 270 ml of methanol and 90 ml of water. The suspension is filtered hot over Celite and the Celite is rinsed several times with methanol. The filtrate is evaporated to dryness and the residue is suspended in water. The solid is filtered off, rinsed with water and dried to yield the title product in the form of orange crystals.

Melting point: 255–260° C.

Elemental microanalysis:

|  | C % | H % | N % |
| --- | --- | --- | --- |
| calculated | 47.22 | 4.88 | 8.47 |
| found | 47.06 | 4.99 | 8.08 |

Step E: 7-Chloro-3-(diethoxyphosphoryl)-2-oxo-1, 2-dihydro-6-quinoline-diazonium tetrafluoroborate The compound obtained in Step D (2.0 g, 6.05 mmol) is added in small portions to a mixture of 4 ml of aqueous 48% $HBF_4$ and 4 ml of water. The suspension is stirred for 10 minutes at room temperature and then at 5° C. in an ice bath. A solution of $NaNO_2$ (416 mg, 6.05 mmol) in 1 ml of water is prepared in parallel. That solution is added to the amine suspension prepared above. The reaction mixture rapidly passes into solution and the reaction mixture is then observed to gain bulk. A little water is added in order to allow stirring, which is continued for 10 minutes. The thick precipitate is then filtered off over a frit and rinsed with a small amount of water. Drying in vacuo in the presence of $P_2O_5$ yields the title diazonium tetrafluoroborate in the form of a beige powder.

Melting point: 184–188° C.

Step F: (7-Chloro-2-oxo-6-phenyl-1,2-dihydro-3-quinolyl)phosphonic acid diethyl ester 500 mg (1.16 mmol) of the compound obtained in Step E, 170 mg (1.39 mmol) of phenylboronic acid and 26 mg (0.11 mmol) of $Pd(OAc)_2$ in a mixture of 40 ml of dioxane and 40 ml of ethanol are stirred overnight. The black solution is evaporated to dryness and the residue is taken up in about 100 ml of ethyl acetate. Black insoluble material is filtered off. The filtrate is washed with water and then with a saturated NaCl solution. Drying is carried out over $MgSO_4$, followed by filtration and evaporation to dryness, the residue is crystallised from diethyl ether and the crystals are filtered off to obtain the title compound after drying.

Melting point: 194° C.

Elemental microanalysis:

|  | C % | H % | N % | Cl % |
| --- | --- | --- | --- | --- |
| calculated | 58.25 | 4.89 | 3.58 | 9.05 |
| found | 58.09 | 4.97 | 3.52 | 9.62 |

EXAMPLE 2

(7-Chloro-2-oxo-6-phenyl-1,2-dihydro-3-quinolyl)-phosphonic acid

The compound obtained in Example 1 (130 mg, 0.33 mmol) is suspended in 10 ml of anhydrous acetonitrile, 0.435 ml (3.3 mmol) of bromotrimethylsilane are added and the mixture is stirred at reflux for 1 hour. Evaporation to dryness is carried out. The residue is dried in vacuo and dissolved in methanol. The solution is stirred for 20 minutes, evaporated to dryness, taken up in acetonitrile, and triturated to obtain a homogeneous precipitate. The white precipitate is filtered off and rinsed with a small amount of acetonitrile and then ether to yield the title compound.

Melting point: >260° C.

Elemental microanalysis:

|  | C % | H % | N % | Cl % |
| --- | --- | --- | --- | --- |
| calculated | 53.67 | 3.30 | 4.17 | 10.56 |
| found | 53.30 | 3.31 | 4.14 | 11.12 |

Examples 3 to 22 are obtained by proceeding as for Examples 1 and 2 starting from the appropriate substrates.

EXAMPLE 3

[7-Chloro-6-(4-nitrophenyl)-2-oxo-1,2-dihydro-3-quinolyl]-phosphonic acid diethyl ester The procedure is as for Example 1, replacing phenylboronic acid in Step F by (4-nitrophenyl)boronic acid pinacolic ester.

Melting point: 256–259° C.

Elemental microanalysis:

|  | C % | H % | N % | Cl % |
| --- | --- | --- | --- | --- |
| calculated | 52.25 | 4.15 | 6.41 | 8.12 |
| found | 52.36 | 4.18 | 6.38 | 8.53 |

EXAMPLE 4

[7-Chloro-6-(4-nitrophenyl)-2-oxo-1,2-dihydro-3-quinolyl]-phosphonic acid

The procedure is as for Example 2 starting from the compound obtained in Example 3.

Melting point: 228° C.

Elemental microanalysis:

|  | C % | H % | N % | Cl % |
| --- | --- | --- | --- | --- |
| calculated | 47.33 | 2.65 | 7.36 | 9.31 |
| found | 47.86 | 2.51 | 7.31 | 9.59 |

EXAMPLE 5

[7-Chloro-6-(3-nitrophenyl)-2-oxo-1,2-dihydro-3-quinolyl]-phosphonic acid diethyl ester The procedure is as for Example 1, replacing phenylboronic acid in Step F by (3-nitrophenyl)boronic acid.

Melting point: 210–212° C.

Elemental microanalysis:

|  | C % | H % | N % | Cl % |
| --- | --- | --- | --- | --- |
| calculated | 52.25 | 4.15 | 6.41 | 8.12 |
| found | 52.24 | 4.19 | 6.21 | 9.66 |

EXAMPLE 6

[7-Chloro-6-(3-nitrophenyl)-2-oxo-1,2-dihydro-3-quinolyl]-phosphonic acid

The procedure is as for Example 2 starting from the compound obtained in Example 5.

Melting point: >310° C.

Elemental microanalysis:

|  | C % | H % | N % | Cl % |
|---|---|---|---|---|
| calculated | 47.33 | 2.65 | 7.36 | 9.31 |
| found | 47.97 | 2.66 | 7.31 | 10.09 |

EXAMPLE 7

(7-Chloro-2-oxo-6-(3-thienyl)-1,2-dihydro-3-quinolyl)-phosphonic acid diethyl ester The procedure is as for Example 1, replacing phenylboronic acid in Step F by (3-thienyl)-boronic acid.

Melting point: 170–172° C.

Elemental microanalysis:

|  | C % | H % | N % | S % | Cl % |
|---|---|---|---|---|---|
| calculated | 51.33 | 4.31 | 3.52 | 8.06 | 8.91 |
| found | 50.93 | 4.21 | 3.69 | 7.32 | 9.56 |

EXAMPLE 8

(7-Chloro-2-oxo-6-(3-thienyl)-1,2-dihydro-3-quinolyl)-phosphonic acid

The procedure is as for Example 2 starting from the compound obtained in Example 7.

Melting point: 245–248° C.

Elemental microanalysis:

|  | C % | H % | N % | S % | Cl % |
|---|---|---|---|---|---|
| calculated | 45.69 | 2.65 | 4.10 | 9.38 | 10.38 |
| found | 45.35 | 2.75 | 4.38 | 9.00 | 11.00 |

EXAMPLE 9

(7-Chloro-6-(1-naphthyl)-2-oxo-1,2-dihydro-3-quinolyl)-phosphonic acid diethyl ester The procedure is as for Example 1, replacing phenylboronic acid in Step F by (1-naphthyl)boronic acid.

Melting point: 224–228° C.

EXAMPLE 10

(7-Chloro-4-(1-naphthyl)-2-oxo-1,2-dihydro-3-quinolyl)-phosphonic acid

The procedure is as for Example 2 starting from the compound obtained in Example 9.

Melting point: >260° C.

Elemental microanalysis:

|  | C % | H % | N % | Cl % |
|---|---|---|---|---|
| calculated | 59.16 | 3.40 | 3.63 | 9.19 |
| found | 58.78 | 3.45 | 3.69 | 8.88 |

EXAMPLE 11

{7-Chloro-2-oxo-6-[4-(trifluoromethyl)phenyl]-1,2-dihydro-3-quinolyl}phosphonic acid diethyl ester The procedure is as for Example 1, replacing phenylboronic acid in Step F by [4-(trifluoromethyl)phenyl]boronic acid.

Melting point: 245–249° C.

Elemental microanalysis:

|  | C % | H % | N % |
|---|---|---|---|
| calculated | 52.25 | 3.95 | 3.05 |
| found | 52.30 | 4.19 | 3.11 |

EXAMPLE 12

{7-Chloro-2-oxo-6-[4-(trifluoromethyl)phenyl]-1,2-dihydro-3-quinolyl}phosphonic acid The procedure is as for Example 2 starting from the compound obtained in Example 11.

Melting point: 245° C.

Elemental microanalysis:

|  | C % | H % | N % | Cl % |
|---|---|---|---|---|
| calculated | 47.61 | 2.50 | 3.47 | 8.78 |
| found | 47.50 | 2.62 | 3.49 | 8.98 |

EXAMPLE 13

[7-Chloro-6-(2-naphthyl)-2-oxo-1,2-dihydro-3-quinolyl]-phosphonic acid diethyl ester The procedure is as for Example 1, replacing phenylboronic acid in Step F by (2-naphthyl)boronic acid.

Melting point: 243–275° C.

Elemental microanalysis:

|  | C % | H % | N % |
|---|---|---|---|
| calculated | 62.52 | 4.79 | 3.17 |
| found | 61.80 | 4.93 | 3.22 |

EXAMPLE 14

[7-Chloro-6-(2-naphthyl)-2-oxo-1,2-dihydro-3-quinolyl]-phosphonic acid

The procedure is as for Example 2 starting from the compound obtained in Example 13.

Melting point: >300° C.

Elemental microanalysis:

|  | C % | H % | N % | Cl % |
|---|---|---|---|---|
| calculated | 59.16 | 3.40 | 3.63 | 9.19 |
| found | 59.02 | 3.46 | 3.61 | 9.54 |

EXAMPLE 15

[7-Chloro-6-(4-methylphenyl)-2-oxo-1,2-dihydro-3-quinolyl]-phosphonic acid diethyl ester The procedure is as for Example 1, replacing phenylboronic acid in Step F by (4-methylphenyl)boronic acid.
Melting point: 259° C.

EXAMPLE 16

[7-Chloro-6-(4-methylphenyl)-2-oxo-1,2-dihydro-3-quinolyl]-phosphonic acid

The procedure is as for Example 2 starting from the compound obtained in Example 15.
Melting point: >300° C.
Elemental microanalysis:

|  | C % | H % | N % | Cl % |
|---|---|---|---|---|
| calculated | 54.95 | 3.75 | 4.01 | 10.14 |
| found | 54.55 | 3.73 | 4.27 | 10.68 |

EXAMPLE 17

(6-[1,1'-Biphenyl]-4-yl-7-chloro-2-oxo-1,2-dihydro-3-quinolyl)phosphonic acid diethyl ester The procedure is as for Example 1, replacing phenylboronic acid in Step F by (1,1'-biphenyl)-4-ylboronic acid.
Melting point: 280–281° C.

EXAMPLE 18

(6-[1,1'-Biphenyl]-4-yl-2-oxo-1,2-dihydro-3-quinolyl)phosphonic acid

The procedure is as for Example 2 starting from the compound obtained in Example 17.
Melting point: >260° C.
Elemental microanalysis:

|  | C % | H % | N % |
|---|---|---|---|
| calculated | 61.25 | 3.67 | 3.40 |
| found | 61.17 | 3.87 | 3.49 |

EXAMPLE 19

[7-Chloro-6-(4-cyanophenyl)-2-oxo-1,2-dihydro-3-quinolyl]-phosphonic acid diethyl ester The procedure is as for Example 1, replacing phenylboronic acid in Step F by (4-cyanophenyl)boronic acid.
Melting point: 273–275° C.

Elemental microanalysis:

|  | C % | H % | N % | Cl % |
|---|---|---|---|---|
| calculated | 57.63 | 4.35 | 6.72 | 8.51 |
| found | 58.03 | 4.46 | 6.91 | 8.89 |

EXAMPLE 20

[7-Chloro-6-(4-cyanophenyl)-2-oxo-1,2-dihydro-3-quinolyl]-phosphonic acid

The procedure is as for Example 2 starting from the compound obtained in Example 19.
Melting point: >260° C.
Elemental microanalysis:

|  | C % | H % | N % | Cl % |
|---|---|---|---|---|
| calculated | 53.28 | 2.79 | 7.77 | 9.83 |
| found | 52.86 | 3.12 | 7.76 | 9.68 |

EXAMPLE 21

[7-Chloro-6-(4-fluorophenyl)-2-oxo-1,2-dihydro-3-quinolyl]-phosphonic acid diethyl ester The procedure is as for Example 1, replacing phenylboronic acid in Step F by (4-fluorophenyl)boronic acid.
Melting point: 228° C.
Elemental microanalysis:

|  | C % | H % | N % |
|---|---|---|---|
| calculated | 55.69 | 4.43 | 3.42 |
| found | 55.03 | 4.84 | 3.51 |

EXAMPLE 22

[7-Chloro-6-(4-fluorophenyl)-2-oxo-1,2-dihydro-3-quinolyl]-phosphonic acid

The procedure is as for Example 2 starting from the compound obtained in Example 21.
Melting point: 265° C.
Elemental microanalysis:

|  | C % | H % | N % | Cl % |
|---|---|---|---|---|
| calculated | 50.94 | 2.85 | 3.96 | 10.02 |
| found | 50.86 | 3.03 | 4.18 | 10.40 |

EXAMPLE 23

[2-Oxo-6-phenyl-7-(trifluoromethyl)-1,2-dihydro-3-quinolyl]phosphonic acid diethyl ester The procedure is as for Example 1, replacing 2-amino-4-chlorobenzaldehyde in Step A by 2-amino-4- trifluoromethylbenzaldehyde, and carrying out the reduction step in Step D with the couple Pd-C/ammonium formate instead of the couple Fe/NH$_4$Cl in a dilute alcoholic medium.

Step A: [(5-Trifluoromethyl-2-formyl-phenylcarbamoyl)methyl]-phosphonic acid diethyl ester Melting point: 62–64° C.
Elemental microanalysis:

|  | C % | H % | N % |
|---|---|---|---|
| calculated | 45.79 | 4.67 | 3.81 |
| found | 45.89 | 4.66 | 3.76 |

Step B: (7-Trifluoromethyl-2-oxo-1,2-dihydro-3-quinolyl)phosphonic acid diethyl ester Melting point: 151° C.
Elemental microanalysis:

|  | C % | H % | N % |
|---|---|---|---|
| calculated | 45.79 | 4.33 | 4.01 |
| found | 48.19 | 4.32 | 3.92 |

Step C: (7-Trifluoromethyl-6-nitro-2-oxo-1,2-dihydro-3-quinolyl)-phosphonic acid diethyl ester Melting point: 209–215° C.
Elemental microanalysis:

|  | C % | H % | N % |
|---|---|---|---|
| calculated | 42.65 | 3.58 | 7.11 |
| found | 42.86 | 3.58 | 6.78 |

Step D: (6-Amino-7-trifluoromethyl-2-oxo-1,2-dihydro-3-quinolyl)-phosphonic acid diethyl ester A mixture of 490 mg (1.24 mmol) of the compound obtained in Step D, 650 mg (12.4 mmol) of ammonium formate and 120 mg of 10% Pd/C in 50 ml of ethanol is stirred at reflux for 1 hour. The catalyst is filtered off over a membrane, the filtrate is evaporated to dryness and the residue is taken up in water. The suspension is filtered, rinsed with water, suction-filtered and dried in vacuo to obtain the title product in the form of a yellow solid.

Melting point: 240–244° C.
Elemental microanalysis:

|  | C % | H % | N % |
|---|---|---|---|
| calculated | 46.16 | 4.43 | 7.69 |
| found | 46.26 | 4.37 | 7.62 |

Step E: 7-Trifluoromethyl-3-(diethoxyphosphoryl)-2-oxo-1,2-dihydro-6-quinoline-diazonium tetrafluoroborate Step F: [2-Oxo-6-phenyl-7-(trifluoromethyl)-1,2-dihydro-3-quinolyl]-phosphonic acid diethyl ester Melting point: 211–214° C.

EXAMPLE 24

(2-Oxo-6-phenyl-7-trifluoromethyl-1,2-dihydro-3-quinolyl]-phosphonic acid

The procedure is as for Example 2 starting from the compound obtained in Example 23.

Melting point: >300° C.
Elemental microanalysis:

|  | C % | H % | N % |
|---|---|---|---|
| calculated | 52.05 | 3.00 | 3.79 |
| found | 51.69 | 2.93 | 3.76 |

EXAMPLE 25

{7-Fluoro-2-oxo-6-[4-(trifluoromethyl)phenyl]-1,2-dihydro-3-quinolyl}phosphonic acid diethyl ester The procedure is as for Example 1, replacing 2-amino-4-chlorobenzaldehyde in Step A by 2-amino-4-fluorobenzaldehyde.

Step A: [(5-Fluoro-2-formyl-phenylcarbamoyl)methyl]phosphonic acid diethyl ester Non-isolated product (oil) used as such in Step B.

Step B: (7-Fluoro-2-oxo-1,2-dihydro-3-quinolyl)phosphonic acid diethyl ester

Melting point: 230–233° C.
Elemental microanalysis:.

|  | C % | H % | N % |
|---|---|---|---|
| calculated | 52.18 | 5.05 | 4.68 |
| found | 52.22 | 5.23 | 4.62 |

Step C: (7-Fluoro-6-nitro-2-oxo-1,2-dihydro-3-quinolyl)phosphonic acid diethyl ester Melting point: 259–262° C.
Elemental microanalysis:

|  | C % | H % | N % |
|---|---|---|---|
| calculated | 45.36 | 4.10 | 8.14 |
| found | 45.40 | 4.28 | 8.06 |

Step D: (6-Amino-7-fluoro-2-oxo-1,2-dihydro-3-quinolyl)phosphonic acid diethyl ester Melting point: 253–257° C.

Elemental microanalysis:

|  | C % | H % | N % |
|---|---|---|---|
| calculated | 49.69 | 5.13 | 8.91 |
| found | 49.52 | 5.28 | 8.70 |

Step E: 7-Fluoro-3-(diethoxyphosphoryl)-2-oxo-1,2-dihydro-6-quinolinediazonium tetrafluoroborate Melting point: 127–131° C.

Step F: {7-Fluoro-2-oxo-6-[4-(trifluoromethyl)phenyl]-1,2-dihydro-3-quinolyl}phosphonic acid diethyl ester Melting point: 258–260° C.
Elemental microanalysis:

|  | C % | H % | N % |
|---|---|---|---|
| calculated | 54.19 | 4.09 | 3.16 |
| found | 54.01 | 4.45 | 3.35 |

EXAMPLE 26

[7-Fluoro-6-(4-trifluoromethylphenyl)-2-oxo-1,2-dihydro-3-quinolyl]phosphonic acid The procedure is as for Example 1 starting from the compound obtained in Example 25.
Melting point: 267° C.
Elemental microanalysis:

|  | C % | H % | N % |
|---|---|---|---|
| calculated | 49.63 | 2.60 | 3.62 |
| found | 50.33 | 2.57 | 3.63 |

EXAMPLE 27

[7-Chloro-2-oxo-6-(1H-pyrrol-1-yl)-1,2-dihydro-3-quinolyl]phosphonic acid diethyl ester A biphasic suspension of 2.43 g (7.35 mmol) of the compound obtained in Step D of Example 1 and 1.33 ml (10.29 mmol) of 2,5-dimethoxytetrahydrofuran in a mixture of 24 ml of distilled water, 12 ml of acetic acid and 36 ml of 1,2-dichloroethane is stirred vigorously at 75° C. for 60 minutes. In TLC ($CH_2Cl_2$/MeOH 9:1), a small amount of starting material is still observed. 0.2 eq. of 2,5-dimethoxytetrahydrofuran (2.06 mmol, 0.26 ml) is added, and heating is maintained for 30 minutes. The mixture is left to return to room temperature and extraction is carried out with $CH_2Cl_2$. The organic phase is washed 4 times with water and then with a saturated NaCl solution. Drying is carried out over $MgSO_4$, followed by evaporation and chromatography of the resulting oil over 200 g of Merck 7734 silica whilst eluting with a mixture of $CH_2Cl_2$/MeOH 95:5. An oil corresponding to the title product is obtained, which is crystallised from isopropyl ether.
Melting point: 193–196° C.

Elemental microanalysis:

|  | C % | H % | N % | Cl % |
|---|---|---|---|---|
| calculated | 53.63 | 4.76 | 7.36 | 9.31 |
| found | 53.92 | 4.89 | 7.28 | 9.55 |

EXAMPLE 28

[7-Chloro-2-oxo-6-(1H-pyrrol-1-yl)-1,2-dihydro-3-quinolyl]-phosphonic acid 3.37 ml (25.5 mmol) of bromotrimethylsilane are added to a solution of the compound obtained in Example 27 (1.62 g, 4.25 mmol) in 30 ml of $CH_2Cl_2$, and the solution is stirred for 4 hours 30 minutes at room temperature. Evaporation to dryness is carried out, and the residue is taken up in methanol. After complete dissolution, a precipitate is observed to form, and stirring is carried out for 10 minutes at room temperature. Filtration and then rinsing with a small amount of methanol and then ether are carried out to obtain the title product.

Melting point: 195–200° C.
Elemental microanalysis:

|  | C % | H % | N % | Cl % |
|---|---|---|---|---|
| calculated | 48.09 | 3.10 | 8.63 | 10.92 |
| found | 48.37 | 3.39 | 7.85 | 10.79 |

EXAMPLE 29

[2-Oxo-6-(1H-pyrrol-1-yl)-7-trifluoromethyl-1,2-dihydro-3-quinolyl]phosphonic acid diethyl ester The procedure is as for Example 27 starting from the compound obtained in Step D of Example 23.
Melting point: 229–234° C.
Elemental microanalysis:

|  | C % | H % | N % |
|---|---|---|---|
| calculated | 52.18 | 4.38 | 6.76 |
| found | 52.23 | 4.42 | 6.73 |

EXAMPLE 30

[2-Oxo-6-(1H-pyrrol-1-yl)-7-trifluoromethyl-1,2-dihydro-3-quinolyl]phosphonic acid A suspension in acetonitrile of 235 mg (0.567 mmol) of the compound obtained in Example 29 and 0.75 ml (5.67 mmol) of bromotrimethylsilane is heated for 1 hour 30 minutes at reflux of the acetonitrile (3 ml). Evaporation to dryness is carried out, the residue is taken up in methanol, and the solution is stirred for 30 minutes and then evaporated to dryness again. The residue is triturated in acetonitrile and the precipitate corresponding to the title product is filtered off.

Melting point: 211–213° C.

Elemental microanalysis:

|  | C % | H % | N % |
|---|---|---|---|
| calculated | 46.94 | 2.81 | 7.82 |
| found | 46.64 | 3.25 | 7.37 |

EXAMPLE 31

6-[4-(Aminosulphonyl)phenyl]-7-chloro-2-oxo-1,2-dihydro-3-quinolylphosphonic acid diethyl ester The procedure is as for Step F of Example 1, replacing phenylboronic acid by 4-sulphamoylphenylboronic acid pinacol ester.

Melting point: 292–295° C.

Elemental microanalysis:

|  | C % | H % | N % | S % | Cl % |
|---|---|---|---|---|---|
| calculated | 48.47 | 4.28 | 5.95 | 6.81 | 7.53 |
| found | 48.80 | 4.44 | 6.50 | 6.58 | 7.40 |

EXAMPLE 32

6-[4-(Aminosulphonyl)phenyl]-7-chloro-2-oxo-1,2-dihydro-3-quinolylphosphonic acid The procedure is as for Example 2 starting from the compound obtained in Example 31.

Melting point: >300° C.

Elemental microanalysis:

|  | C % | H % | N % | S % | Cl % |
|---|---|---|---|---|---|
| calculated | 43.44 | 2.92 | 6.75 | 7.73 | 8.55 |
| found | 43.12 | 2.84 | 6.61 | 7.50 | 8.38 |

Pharmacological Study

EXAMPLE A

Inhibition of the Current Induced by Administration of (R,S)-AMPA (10 μM) to *Xenopus oocytes* Injected with mRNAs of Rat Cortex

*Xenopus oocytes* are injected with 50 ng of poly (A+) mRNAs isolated from the cerebral cortex of rat and incubated for 2 to 3 days at 18° C. to enable their protein expression. The influx currents induced by an administration of (R,S)-AMPA (10 μM) are measured in a medium having the composition: NaCl (82.5 mM), KCl (2.5 mM), $CaCl_2$ (1 mM), $MgCl_2$ (1 mM), $NaH_2PO_4$ (1 mM), HEPES (5 mM), pH 7.4, by the 2-electrode voltage clamp method (potential=–60 mV). The products of the present invention are administered in a concentration-dependent manner 30 seconds before and during administration of the agonist (R,S)-AMPA. Their capacity to inhibit the current induced by (R,S)-AMPA is determined by the $IC_{50}$ values (μM), which represent the concentrations that inhibit by 50% the current induced by an administration of (R,S)-AMPA (10 μM). The compounds of the invention demonstrate excellent inhibitory properties with $IC_{50}$ values (μM) of the order of 1.

EXAMPLE B

Audiogenic Convulsion Test in the DBA/2 Mouse

In the immature DBA/2 mouse, convulsive attacks can be triggered by subjecting the animal to stimulation with high-intensity high-frequency sound. The AMPA-type glutamate receptor antagonists antagonise that type of convulsion in a dose-dependent manner (Chapman et al., Epilepsy Res., 1991, 9, 92–96). This test is used to study the anti-convulsive effects of the compounds of the present invention. In brief, immature DBA/2 mice (21–28 days) are exposed for 60 seconds to a noise of 105 dB and 18 kHz. This causes the appearance of clonic convulsions. The products being studied and the solvent are administered by the i.p. route 30 minutes before the start of the test in a volume of 0.1 ml/10 g. The $ED_{50}$ value (dose that inhibits the occurrence of the convulsions by 50%) is determined for each compound using the method of Litchfield and Wicoxon (J. Pharmacol. Exp. Ther., 1949, 96, 99–113). The compounds of the invention demonstrate an excellent capacity to inhibit the convulsions with $ED_{50}$ values of the order of 10 mg/kg ip.

EXAMPLE C

Pharmaceutical Composition 1000 tablets containing a dose of 5 mg of {7-chloro-2-oxo-6-[4-(trifluoromethyl)phenyl]-1,2-dihydro-3-quinolyl}phosphonic
acid (Example 12) 5 g
Wheat starch 20 g
Maize starch 20 g
Lactose 30 g
Magnesium stearate 2 g
Silica 1 g
Hydroxypropylcellulose 2 g

We claim:

1. A compound selected from those of formula (I):

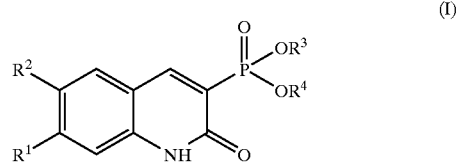

wherein:

$R^1$ represents halogen or trifluoromethyl, $R^2$ represents aryl or heteroaryl, $R^3$ and $R^4$, which may be identical or different, represent hydrogen or alkyl, cycloalkyl, aryl or arylalkyl or a group

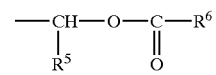

(wherein $R^5$ and $R^6$, which may be identical or different, represent hydrogen or alkyl, cycloalkyl or aryl), it being understood that:

"alkyl" is understood to mean linear or branched alkyl containing 1 to 6 carbon atoms, "cycloalkyl" is understood to mean cyclic alkyl containing 3 to 8 carbon atoms, "aryl" is understood to mean the groups phenyl, naphthyl or biphenyl, it being possible for those groups to be unsubstituted or substituted by 1 to 3 groups selected from alkyl, cycloalkyl, alkoxy, polyhaloalkyl, cyano, nitro, amino, alkylamino, dialkylamino, $SO_2NR^7R^8$ (wherein $R^7$ and $R^8$, which may be identical or different, represent hydrogen or alkyl, cycloalkyl or aryl) and halogen atoms, "heteroaryl" is understood to mean a mono-cyclic aromatic group containing 5 to 6 ring atoms and containing 1 to 3 heteroatoms selected from oxygen, nitrogen and sulphur, it being possible for the heteroaryl to be attached to the benzene ring that carries it by carbon or by nitrogen when it has one, and for it to be unsubstituted or substituted by 1 to 3 groups selected from alkyl, alkoxy, polyhaloalkyl, cyano, nitro, amino (unsubstituted or substituted by 1 or 2 alkyl groups), $SO_2NR^7R^8$ (wherein $R^7$ and $R^8$ are as defined hereinbefore) and halogen atoms, its enantiomers and diastereoisomers and addition salts thereof with a pharmaceutically acceptable acid or base.

2. A compound of claim 1 wherein $R^1$ represents chlorine or $CF_3$.

3. A compound of claim 1 wherein $R^2$ represents unsubstituted or substituted naphthyl, phenyl or biphenyl.

4. A compound of claim 1 wherein $R^2$ represents pyrrole or thiophene.

5. A compound of claim 1 wherein $R^3$ and $R^4$ simultaneously represent hydrogen.

6. A compound of claim 1 selected from {7-chloro-2-oxo-6-[4-(trifluoromethyl)phenyl]-1,2-dihydro-3-quinolyl}phosphonic acid and [7-chloro-6-(4-methylphenyl)-2-oxo-1,2-dihydro-3-quinolyl]phosphonic acid, their isomers and addition salts thereof with a pharmaceutically acceptable base.

7. A method for treating an animal or human living body afflicted with acute and chronic pathological condition associated with hyperactivation of the excitatory amino acid neurotransmission pathways to comprising the step of administering to the living body an amount of a compound of claim 1 which is effective for alleviation of said condition.

8. A method for treating an animal or human living body afflicted with cerebrovascular accident, cerebral or spinal trauma, epilepsy, chronic neurodegenerative diseases comprising the step of administering to the living body an amount of a compound of claim 1 which is effective for alleviation of said condition.

9. A pharmaceutical composition useful in the method for treating an animal or human living body afflicted with acute and chronic pathological condition associated with hyperactivation of the excitatory amino acid neurotransmission pathways comprising as active principle an effective amount of a compound as claimed in claim 1, together with one or more pharmaceutically acceptable excipients or vehicles.

10. A pharmaceutical composition useful in the method for treating an animal or human living body afflicted with cerebrovascular accident, cerebral or spinal trauma, epilepsy, chronic neurodegenerative diseases comprising as active principle an effective amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,420,386 B1
DATED : July 16, 2002
INVENTOR(S) : Alex Cordi et al.

It is certified that error appears in the above-identified patent and that said Letters Patent is hereby corrected as shown below:

Title page,
Item [54], "QUINOLYLPHOSPHONIC" should read -- QUINOLYNYLPHOSPHONIC --.
Item [73], "Laboratories" should read -- Laboratoires --.

Column 20,
Line 6, please delete the word "to".

Signed and Sealed this

Fifth Day of November, 2002

Attest:

Attesting Officer

JAMES E. ROGAN
Director of the United States Patent and Trademark Office